United States Patent
Miller

(10) Patent No.: US 7,142,913 B2
(45) Date of Patent: Nov. 28, 2006

(54) DEFIBRILLATOR TEST DEVICE AND METHOD

(75) Inventor: James L. Miller, Westford, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 446 days.

(21) Appl. No.: 10/729,652

(22) Filed: Dec. 5, 2003

(65) Prior Publication Data
US 2004/0116968 A1 Jun. 17, 2004

Related U.S. Application Data

(60) Provisional application No. 60/432,799, filed on Dec. 12, 2002.

(51) Int. Cl.
*A61N 1/37* (2006.01)

(52) U.S. Cl. .......................................................... 607/5
(58) Field of Classification Search .................... 607/5; 338/258, 333, 334
See application file for complete search history.

(56) References Cited

U.S. PATENT DOCUMENTS 6,156,450 A * 12/2000 Bailey .......................... 429/93

* cited by examiner

*Primary Examiner*—Scott M. Getzow
(74) *Attorney, Agent, or Firm*—Tony Piotrowski

(57) ABSTRACT

A defibrillator test device is disclosed that uses a temperature response as an indication of a test result. The defibrillator test device receives electrical energy from a defibrillation pulse and converts the electrical energy into heat in a resistive member. The heat raises the temperature of the resistive member. A visual test result indication is provided in response to a temperature increase of the resistive member.

18 Claims, 1 Drawing Sheet

DEFIBRILLATOR TEST DEVICE AND METHOD

This application claims the benefit of U.S. Provisional Application Ser. No. 60/432,799, filed on Dec. 12, 2002.

The present invention relates to the field of test equipment. More particularly, the invention relates to a defibrillator test device that uses a temperature response to provide a test result indication.

Electro-chemical activity within a human heart normally causes the heart muscle fibers to contract and relax in a synchronized manner that results in the effective pumping of blood from the ventricles to the body's vital organs. Sudden cardiac death is often caused by ventricular fibrillation (VF) in which abnormal electrical activity within the heart causes the individual muscle fibers to contract in an unsynchronized and chaotic way. The only effective treatment for VF is electrical defibrillation in which an electrical shock is applied to the heart to allow the heart's electro-chemical system to re-synchronize itself. Once organized electrical activity is restored, synchronized muscle contractions usually follow, leading to the restoration of cardiac rhythm.

A defibrillator is an electrical device that is used to restart the heart of a patient that is in fibrillation. There are a variety of different types of defibrillators, e.g., external and patient-implantable.

At the completion of open chest surgery when the patient is removed from the heart-lung bypass machine an electrical shock is frequently needed. The surgeon inserts two paddle electrodes into the patient's chest. The paddles have electrodes that are placed in contact with the patient's heart. A defibrillation shock is administered to the heart that "resynchronizes" the heart causing it to beat normally. The paddle electrodes must be sterile to prevent infection. Repeated sterilization and repeated use cause the paddles to degrade over time.

It is critically important that the therapeutic shock be administered to the heart in a timely manner. The defibrillator, the paddles, cables, and controls must be in good working order before they are needed to defibrillate the heart. Therefore, it is desirable to test and confirm the proper function of all elements in the therapy shock delivery chain including the defibrillator, paddles, connectors, connecting wires, and switch(s) oft en prior to use.

A common test method is to connect the paddle electrodes to a tester and to deliver a test shock. At least in the case of internal paddle electrodes, they must be sterile. Anything coming into contact with them must also be sterile or contamination will result.

Conventional reusable defibrillator testers must be sterilized between each use. Such reusable defibrillator testers must be robust to withstand the rigors of sterilization and consequentially expensive. In addition, the cost of the sterilization process adds to the cost of ownership.

Conventional single use disposable sterile testers are also known. However, these convention single use disposable testers have not been practical due to their cost. In this regard, since they are discarded after each use the cost is a very important consideration.

Conventional current testers are also known. These devices use electrical circuits containing neon or other types of lamps that flash momentarily when a defibrillator voltage is applied. These circuits are voltage sensitive. Since the lamps only flash momentarily, it is easy to miss the brief flash of light, especially in bright ambient light. In addition, these circuits are relatively expensive and don't indicate the quality or energy level of the discharge.

Accordingly, there exists a need for improved, cost-effective, defibrillator test devices.

The present invention addresses the foregoing need by providing an improved, cost-effective, defibrillator test device.

One aspect of the present invention is directed to using a temperature response as an indication of a test result. In this aspect, the test device receives electrical energy from a defibrillation pulse and converts the electrical energy into heat in a resistive member. The heat raises the temperature of the resistive member. The temperature increase is a function of the defibrillator energy delivered. A visual indicator is provided in contact with the resistive member. The visual indicator indicates an increase in temperature of the resistive member.

The temperature indication may be permanent or reversible. The temperature indicator may provide an analog indication of temperature or indicate that a temperature threshold has been exceeded. The temperature response is calibrated to an approved or desired energy input.

Various embodiments of the present invention have one or more of the following advantages: inexpensive to manufacture, no circuitry to reduce reliability, energy sensitive rather than voltage sensitive, can be designed for a single use or for multiple use and/or the indication lasts for several seconds or can be permanent.

One embodiment of the present invention is directed to a defibrillator test device including an electrical resistive material, at least two contact areas electrically connected to the electrical resistor, and a temperature reactive material in contact with the electrical resistive material.

Another embodiment of the present invention is directed to a method of testing a defibrillator. The method includes the steps of connecting the defibrillator to a test device, discharging an electrical signal through the test device and providing a result indication in response to a temperature change of the test device.

This brief summary has been provided so that the nature of the invention may be understood quickly. A more complete understanding of the invention can be obtained by reference to the following detailed description of the preferred embodiments thereof in connection with the attached drawings.

Figure 1:
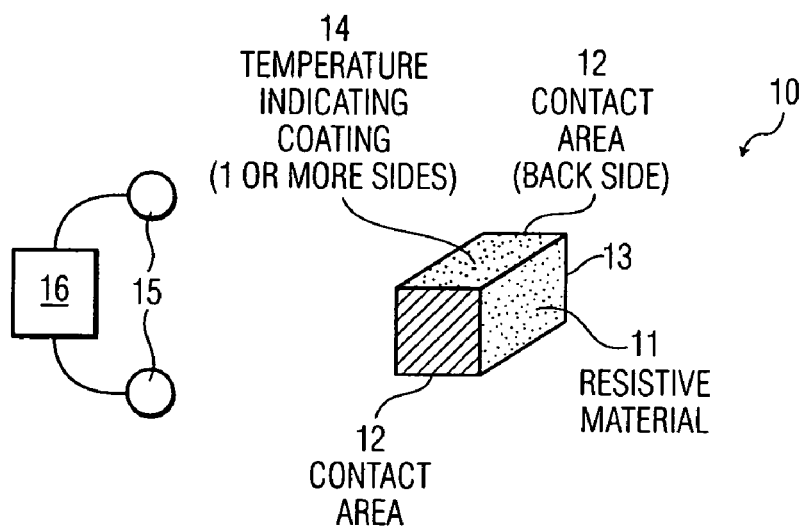
FIG. 1 depicts a test device in accordance with one embodiment of the present invention.

FIG. 1 shows a first embodiment of the present invention. A defibrillator test device 10 includes an electrical resistor 11. The electrical resistor 11 may be a two-dimensional pattern of resistive material in the shape of a rectangle, a square, a circle, a triangle, a polygon, or other shape. The electrical resistor 11 may also be a three-dimensional solid in the shape of a cube, rectangular solid, a sphere, a cylinder, or other shape. It should be understood that any shape can be used for the electrical resistor 11.

The electrical resistor 11 has at least two conductive electrical contact surfaces 12. These contact surfaces are preferably at opposite ends of the electrical resistor 11. These contact surfaces 12 are used to make electrical contact with the defibrillator paddles. A defibrillator pad connector/interface may also be used in conjunction or in place of the contract surfaces 12. One or more of the remaining side(s)

13 of the electrical resistor 11 are coated with a material 14 that indicates temperature and/or reacts to a change in temperature.

In one embodiment, the material 14 is a reversible temperature sensitive liquid crystal paint (TSP). The TSP can be used, for example, to measure the surface temperature of items with unusual shapes. The TSP may be applied by brush directly to the electrical resistor's 11 surfaces.

Some thermal liquid crystal paints utilizes a fluorescence process of organic luminophores suspended in a polymeric binder. A luminophore molecule is excited by absorbing a photon (light). The molecule may then transition back to a ground state by emitting the absorbed photon (in the form of fluorescence). If a binder such as oxygen-impermeable is used, the temperature-dependent, non-radiative deactivation becomes the primary source of fluorescence suppression and the rate of fluorescence emission is dominated by temperature. As a result, the intensity of TSP fluorescence is inversely proportional to temperature.

The TSP is also available as water-soluble paints. Such TSP's contain microencapsulated nontoxic cholesteryl ester-based liquid crystals that change color (e.g., from reddish-brown to green to blue) as the temperature increases. The color change reverses itself when the temperature decreases so that the change can be observed repeatedly.

The color changes are best seen on a dark background. In this regard, a black backing paint may be applied first to the electrical resistor 11.

The energy range of a therapeutic defibrillator shock when applied directly to the heart is 0 to 50 Joules. The range for transthoracic shock is typically 100 to 360 Joules. When testing a defibrillator this energy is transferred to the resistive material. In this regard, preferably, the resistive value (Ohm) of the electrical resistor 11 is in the range of 10 to 200 Ohms. The resistive value used will be determined by making the electrical resistance of the resistor equal to the nominal resistance of the electrical path through the patient.

The energy delivered to the resistor is in the form of a short electrical pulse. The time duration of the pulse is short, typically less then 15 msec. The temperature rise of the resistive material is dependent on the energy delivered because the process is adiabatic during the short delivery interval and for several seconds following the delivery. The temperature rise of the resistor can therefore be controlled by adjusting the thermal mass of the resistor and heat capacity of the resistive material. The temperature rise can therefore be set to provide a clear thermal response but not high enough to cause possible burns to an operator or observer. Various temperature range indicators may be used depending on the particular defibrillator to be tested.

The shock delivery specifications for a particular defibrillator is a given. Thus, by taking the above factors into consideration, appropriate resistive values for the electric resistor 11 and appropriate temperature ranges of the TSP can be determined for any defibrillator to be tested.

In operation, electrodes, an energy delivery interface or paddles 15 associated with a defibrillator 16 to be tested are placed in electrical contact with the contact surfaces 12. The defibrillator 16 is then triggered to release energy (e.g., in the form of an electrical signal) via the contact surfaces 12 through the electrical resistor 11. The material 14 will then provide a visual indication as to a test result.

For example, if the appropriate amount of energy (based upon the defibrillator's technical specifications) is released by the defibrillator, the visual indication can be a color change in the material 14. As discussed above, the color change may be gradual or change once a threshold temperature is reached by the electrical resistor 11.

As also discussed above, the value of the resistor 11 and the TSP temperature range are selected to provide an appropriate color change based upon a predetermined appropriate amount of energy. The material 14 may change different colors in response to different energy amounts released from the defibrillator 16. In this regard, the defibrillator test device 10 may be calibrated to provide certain color changes in response to predetermined energy discharges from the defibrillator 16.

As the heat energy dissipates from the electrical resistor 11, the material 14 will return to its original state. This allows the defibrillator test device 10 to be used again.

Figure 2:
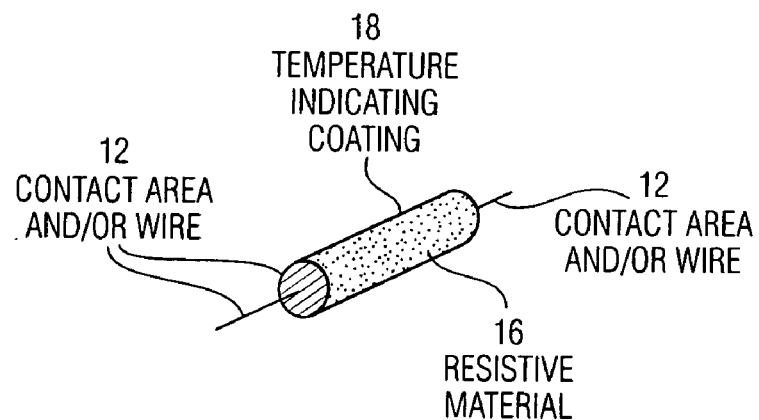
FIG. 2 depicts a test device in accordance with a second embodiment of the present invention.

In another embodiment, as shown in FIG. 2, a coating material 18 may be applied to the electrical resistor 11. The coating material 18 may be an opaque wax paint material, or similar material, that melts in response to a rise in temperature of the electrical resistor 11. As the coating material 18 melts a visual indication is revealed. For example, the coating material 18 may be a white wax that turns clear as it melts to reveal a black paint under coating that then becomes visible. This would provide a permanent visual indication. The coating material 18 may be reapplied to allow the defibrillator test device 10 to be reused.

In yet another embodiment, the electrical resistor 11 is coated with a chemical indicator that provides a permanent indication. The chemical indicator, for example, may be similar to those used in thermal recorder paper. An indicating material 14 with different temperature thresholds may be applied to each different surfaces of the electrical resistor. This would enable the defibrillator test device 10 to provide a test indication for different defibrillation pulse energies.

Figure 3:
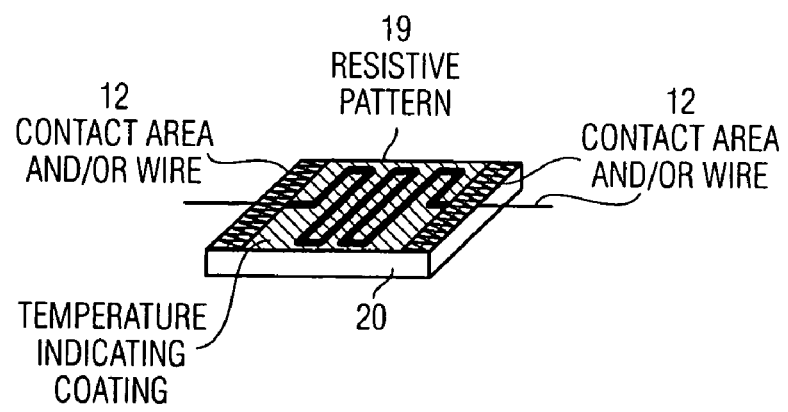
FIG. 3 depicts a test device in accordance with a third embodiment of the present invention.

FIG. 3 shows another embodiment the present invention. A resistive material 19 is screen printed on an insulating substrate 20. The resistive material 19 may also be applied in a particular pattern or word(s), e.g., DEFIBRILLATOR-TESTER. Electrically conductive contacts 12 are attached to the resistive material 19. As discussed above, the contacts 12 are used to make electrical contact with the defibrillator paddles 15. The resistive material 19 may then be coated with the same temperature indicating materials 14 described above.

The material 14 may also be applied on the electrical resistor 11 or the resistive material 19 so that a particular pattern or word is depicted for a positive test result. For example, rather than a simple color change, the word "pass", "good" or "OK" may be indicated by the color change.

The temperature response principles (i.e., using temperature reactive materials such as TSP, wax and chemical indicators) of the present invention as described in the embodiments above may also be applied using a mechanical device. For example, a switch that activates or pops-up in response/reacts to temperature changes may also be used as the visual indication.

In this regard, the present invention has been described with respect to particular illustrative embodiments. It is to be understood that the invention is not limited to the above-described embodiments and modifications thereto, and that various changes and modifications may be made by those of ordinary skill in the art without departing from the spirit and scope of the appended claims.

The invention claimed is:

1. A defibrillator test device for testing a defibrillator which delivers an electrical pulse through electrodes, comprising:

an electrical resistive material, at least two contact areas electrically connected to the resistive material and to the defibrillator electrodes during testing, and a temperature reactive material in contact with the electrical resistive material which reacts in response to delivery of an electrical pulse by the defibrillator.

2. The defibrillator test device according to claim 1, wherein the electrical resistive material has a resistive value between 10 and 200 ohms.

3. The defibrillator test device according to claim 1, wherein, the at least two contact areas are arranged to receive energy from a defibrillator.

4. The defibrillator test device according to claim 1, wherein the temperature reactive material is a thermal liquid crystal paint.

5. The defibrillator test device according to claim 1, wherein the temperature reactive material is a material that changes state.

6. The defibrillator test device according to claim 1, wherein the temperature reactive material is a material that experiences a chemical reaction.

7. The defibrillator test device according to claim 1, wherein the temperature reactive material includes a mechanical device.

8. The defibrillator test device according to claim 1, wherein the electrical resistive material is a resistor.

9. The defibrillator test device according to claim 1, wherein the temperature reactive material provides a visual indication in response to a change in temperature of the resistive material.

10. The defibrillator test device according to claim 9, wherein in the visual indication is temporary.

11. The defibrillator test device according to claim 9, wherein in the visual indication is permanent.

12. The defibrillator test device according to claim 9, wherein in the visu al indication may be manuallu reset.

13. The defibrillator test device according to claim 9, wherein the temperature reactive material provides a predetermined visual indication in response to delivery of an electrical pulse of a predetermined amount of energy by the defibrillator.

14. The defibrillato r test device according to claim 13, wherein the predetermined visual indication comprises a predetermined color change.

15. The defibrillator test device according to claim 9, wherein the electrical pulse and the visual indication each have a duration, wherein the duration of the visual indication exceeds the duration of the electrical pulse.

16. The defibrillator test device according to claim 1, wherein the electrodes further comprise paddle electrodes.

17. A defibrillator test device for testing a defibrillator which delivers an electrical pulse through electrodes, comprising:

means for receiving an electrical pulse from the defibrillator and exhibiting a temperature change in response to the pulse; and means, coupled to the pulse receiving means, for providing a test result, in response to the electrical pulse, in accordance with the temperature change.

18. A method of testing a defibrillator, comprising the steps of:

connecting the defibrillator to a test device;

discharging an electrical signal through the test device;

providing a result indication in response to a temperature change of the test device.

* * * * *